(12) United States Patent
Schroeder et al.

(10) Patent No.: US 7,462,318 B2
(45) Date of Patent: *Dec. 9, 2008

(54) CROSSLINKED POLYMERIC MATERIAL WITH ENHANCED STRENGTH AND PROCESS FOR MANUFACTURING

(75) Inventors: David W. Schroeder, Winona Lake, IN (US); Jordan H. Freedman, Fort Wayne, IN (US); James E. Gunter, Claypool, IN (US); Brian D. Salyer, Warsaw, IN (US); H. Gene Hawkins, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 316 days.

This patent is subject to a terminal disclaimer.

(21) Appl. No.: 10/963,975

(22) Filed: Oct. 13, 2004

(65) Prior Publication Data

US 2006/0079596 A1    Apr. 13, 2006

Related U.S. Application Data

(60) Provisional application No. 60/616,811, filed on Oct. 7, 2004.

(51) Int. Cl.
*B29C 47/00* (2006.01)
*C08J 5/00* (2006.01)
*C08J 3/28* (2006.01)

(52) U.S. Cl. .................. 264/323; 264/331.17; 264/346; 522/161

(58) Field of Classification Search ................. 522/161; 264/323, 346, 331.17, 344, 348
See application file for complete search history.

(56) References Cited

U.S. PATENT DOCUMENTS

| | | | |
|---|---|---|---|
| 2,948,666 A | 8/1960 | Lawton | |
| 3,362,897 A | 1/1968 | Lawton | |
| 3,563,870 A | 2/1971 | Tung et al. | |
| 3,886,056 A | 5/1975 | Kitamaru et al. | |
| 3,956,253 A | 5/1976 | Braun | |
| 4,055,862 A | 11/1977 | Farling | |
| 4,171,338 A | 10/1979 | Mason | |
| 4,224,696 A | 9/1980 | Murray et al. | |
| 4,281,420 A | 8/1981 | Raab | |
| 4,348,350 A * | 9/1982 | Meier et al. ................. | 264/570 |
| 4,390,666 A | 6/1983 | Moriguchi et al. | |
| 4,582,656 A | 4/1986 | Hoffman | |
| 4,586,995 A | 5/1986 | Randall et al. | |
| 4,587,163 A | 5/1986 | Zachariades | |
| 4,636,340 A | 1/1987 | Itaba et al. | |
| 4,655,769 A | 4/1987 | Zachariades | |
| 4,668,577 A | 5/1987 | Ohta et al. | |
| 4,747,990 A | 5/1988 | Gaussens et al. | |
| 4,778,633 A * | 10/1988 | Kiang et al. ................. | 264/470 |
| 4,902,460 A | 2/1990 | Yagi et al. | |
| 5,030,402 A | 7/1991 | Zachariades | |
| 5,030,487 A | 7/1991 | Rosenzweig | |
| 5,037,928 A | 8/1991 | Li et al. | |
| 5,066,755 A | 11/1991 | Lemstra | |
| 5,130,376 A | 7/1992 | Shih | |
| 5,160,464 A | 11/1992 | Ward et al. | |
| 5,200,439 A | 4/1993 | Asanuma | |
| 5,204,045 A | 4/1993 | Courval et al. | |
| 5,210,130 A | 5/1993 | Howard, Jr. | |
| 5,234,652 A * | 8/1993 | Woodhams et al. ...... | 264/210.2 |
| 5,276,079 A | 1/1994 | Duan et al. | |
| 5,358,529 A | 10/1994 | Davidson | |
| 5,405,393 A | 4/1995 | Falkenström | |
| 5,414,049 A | 5/1995 | Sun et al. | |
| 5,428,079 A | 6/1995 | Bastiaansen et al. | |
| 5,439,949 A | 8/1995 | Lucas et al. | |
| 5,449,745 A | 9/1995 | Sun et al. | |
| 5,466,530 A | 11/1995 | England et al. | |
| 5,478,906 A | 12/1995 | Howard, Jr. | |
| 5,505,900 A | 4/1996 | Suwanda et al. | |

(Continued)

FOREIGN PATENT DOCUMENTS

CA    1 257 745    7/1989

(Continued)

OTHER PUBLICATIONS

"Researchers Get Awards for Orthopaedic Research", The American Academy of Orthopaedic Surgeons, News Release. (Mar. 19, 1998), available at http://www.aaos.org/wordhtml/press/98press/kappa.htm. (4 pages).

(Continued)

*Primary Examiner*—Susan W Berman
(74) *Attorney, Agent, or Firm*—Harness, Dickey & Pierce, P.L.C.

(57) ABSTRACT

A radiation crosslinked (50 kGy), pressure-treated UHMWPE material has been developed by applying compressive force on a crosslinked polymer in a direction orthogonal to an axial direction. The deformed material is then cooled while held in a deformed state. The resulting material is anisotropic, with enhanced strength oriented along the axial direction. The directionally engineered material is oxidatively stable even after four weeks of accelerated aging in a pressure vessel containing five atmospheres of oxygen (ASTM F2003). Because of its oxidative stability, the deformation processed material is a suitable candidate for air-permeable packaging and gas sterilization, which has thus far been reserved for remelted highly crosslinked UHMWPEs.

39 Claims, 3 Drawing Sheets

U.S. PATENT DOCUMENTS

| | | | |
|---|---|---|---|
| 5,508,319 | A | 4/1996 | DeNicola, Jr. et al. |
| 5,543,471 | A | 8/1996 | Sun et al. |
| 5,552,104 | A | 9/1996 | DeNicola, Jr. et al. |
| 5,577,368 | A | 11/1996 | Hamilton et al. |
| 5,650,485 | A | 7/1997 | Sun et al. |
| 5,684,124 | A | 11/1997 | Howard, Jr. et al. |
| 5,709,020 | A | 1/1998 | Pienkowski et al. |
| 5,728,748 | A | 3/1998 | Sun et al. |
| 5,824,411 | A | 10/1998 | Shalaby et al. |
| 5,879,400 | A | 3/1999 | Merrill et al. |
| 6,017,975 | A | 1/2000 | Saum et al. |
| 6,048,480 | A | 4/2000 | Doyle |
| 6,143,232 | A | 11/2000 | Rohr |
| 6,146,426 | A | 11/2000 | Doyle |
| 6,165,220 | A | 12/2000 | McKellop et al. |
| 6,168,626 | B1 | 1/2001 | Hyon et al. |
| 6,174,934 | B1 | 1/2001 | Sun et al. |
| 6,184,265 | B1 | 2/2001 | Hamilton et al. |
| 6,228,900 | B1 | 5/2001 | Shen et al. |
| 6,242,507 | B1 | 6/2001 | Saum et al. |
| 6,245,276 | B1 | 6/2001 | McNulty et al. |
| 6,281,264 | B1 | 8/2001 | Salovey et al. |
| 6,316,158 | B1 | 11/2001 | Saum et al. |
| 6,355,215 | B1 | 3/2002 | Poggie et al. |
| 6,365,089 | B1 | 4/2002 | Krebs et al. |
| 6,372,814 | B1 | 4/2002 | Sun et al. |
| 6,395,799 | B1 | 5/2002 | Johnson |
| 6,432,349 | B1 | 8/2002 | Pletcher et al. |
| 6,458,727 | B1 | 10/2002 | Jones et al. |
| 6,464,926 | B1 | 10/2002 | Merrill et al. |
| 6,494,917 | B1 | 12/2002 | McKellop et al. |
| 6,503,439 | B1 | 1/2003 | Burstein |
| 6,547,828 | B2 | 4/2003 | Scott et al. |
| 6,562,540 | B2 | 5/2003 | Saum et al. |
| 6,641,617 | B1 | 11/2003 | Merrill et al. |
| 6,664,308 | B2 | 12/2003 | Sun et al. |
| 6,686,437 | B2 | 2/2004 | Buchman et al. |
| 6,692,679 | B1 | 2/2004 | McNulty et al. |
| 6,709,464 | B2 | 3/2004 | Scott et al. |
| 6,726,727 | B2 | 4/2004 | Scott et al. |
| 6,786,933 | B2 | 9/2004 | Merrill et al. |
| 6,800,670 | B2 | 10/2004 | Shen et al. |
| 6,818,020 | B2 | 11/2004 | Sun et al. |
| 6,818,172 | B2 | 11/2004 | King et al. |
| 6,852,772 | B2 | 2/2005 | Muratoglu et al. |
| 6,905,511 | B2 | 6/2005 | Wang et al. |
| 2001/0049401 | A1 | 12/2001 | Salovey et al. |
| 2002/0007219 | A1 | 1/2002 | Merrill et al. |
| 2002/0156536 | A1 | 10/2002 | Harris et al. |
| 2003/0013781 | A1 | 1/2003 | Merrill et al. |
| 2003/0045603 | A1 | 3/2003 | Salovey et al. |
| 2003/0105182 | A1 | 6/2003 | Merrill et al. |
| 2003/0119935 | A1 | 6/2003 | Merrill et al. |
| 2003/0125513 | A1 | 7/2003 | King |
| 2003/0137081 | A1 | 7/2003 | Pitkanen |
| 2003/0139555 | A1 | 7/2003 | Hubbard et al. |
| 2003/0158287 | A1 | 8/2003 | Salovey et al. |
| 2003/0208278 | A1 | 11/2003 | Richard |
| 2003/0212161 | A1 | 11/2003 | McKellop et al. |
| 2003/0229155 | A1 | 12/2003 | Wang et al. |
| 2004/0132856 | A1 | 7/2004 | Merrill et al. |
| 2004/0208841 | A1 | 10/2004 | Salovey et al. |
| 2004/0266902 | A1 | 12/2004 | Shen et al. |
| 2005/0006821 | A1 | 1/2005 | Merrill et al. |
| 2005/0010288 | A1 | 1/2005 | Merrill et al. |
| 2005/0043431 | A1 | 2/2005 | Wang et al. |
| 2005/0043815 | A1 | 2/2005 | King et al. |
| 2005/0048096 | A1 | 3/2005 | Shen et al. |
| 2005/0056971 | A1 | 3/2005 | Merrill et al. |
| 2005/0059750 | A1 | 3/2005 | Sun et al. |
| 2005/0069696 | A1 | 3/2005 | King et al. |
| 2005/0096749 | A1 | 5/2005 | Merrill et al. |

FOREIGN PATENT DOCUMENTS

| | | |
|---|---|---|
| EP | 0 729 981 B1 | 3/2002 |
| JP | 57-211347 | 12/1982 |
| JP | 62-243634 | 10/1987 |
| JP | 02-175137 | 7/1990 |
| JP | 04-198201 | 7/1992 |
| JP | 05-507748 | 11/1993 |
| JP | 91 022222 | 5/1997 |
| WO | WO 93/10953 | 6/1993 |
| WO | WO 95/06148 | 3/1995 |
| WO | WO 98/01085 | 1/1998 |
| WO | WO 98/14223 | 4/1998 |
| WO | WO 03/049930 | 6/2003 |

OTHER PUBLICATIONS

"Researchers to Get Kappa Delta Awards for Achievements" The American Academy of Orthopaedic Surgeons, Academy News. (Mar. 19, 1998), available at http://www.aaos.org/wordhtml/98news/kappa.htm. (3 pages).

Appleby et al. "Post-Gamma Irradiation Cross-linking of Polyethylene Tape by Acetylene Treatment" Journal of Materials Science. vol. 29 (1994) p. 227-231.

Appleby et al. "Property Modification of Polyethylene Tapes by Acetylene-Sensitized Gamme Irradiation" Journal of Materials Science. vol. 29 (1994) p. 151-156.

Bhateja et al. "Radiation-Induced Crystallinity Changes in Polyethylene Blends" Journal of Materials Science. vol. 20 (1985) p. 2839-2845.

Bhateja, S. "Radiation-Induced Crystallinity Changes in Linear Polyethylene" Journal of Polymer Science: Polymer Physics Edition. vol. 21 (1983) p. 523-536.

Bhateja, S. "Radiation-Induced Crystallinity Changes in Linear Polyethylene: Influence of Aging" Journal of Applied Polymer Science. vol. 28 (1983) p. 861-872.

Bhateja, S. "Radiation-Induced Crystallinity Changes in Pressure-Crystallized Ultrahigh Molecular Weight Polyethylene" J. Macromol. Sci. Phys. B22(1) (1983) p. 159-168.

Bowman, J. "The Processing and Properties of γ-Irradiated HDPE Granules" Intern. Polymer Processing III. (1988) p. 211-220.

Chen et al. "Radiation-Induced Crosslinking: II. Effect on the Crystalline and Amorphous Densities of Polyethylene" Colloid Polym Sci. vol. 269 (1991) p. 469-476.

Chen et al. "Radiation-Induced Crosslinking: III. Effect on the Crystalline and Amorphous Density Fluctuations of Polyethylene" Colloid Polym Sci. vol. 269 (1991) p. 353-363.

Choudhury et al. "The Effects of Irradiation and Ageing on the Abrasive Wear Resistance of Ultra High Molecular Weight Polyethylene" Wear Elsevier Science. vol. 203-204 (1997) p. 335-340.

Chu et al. "Some Structures and Properties of Very High Molecular Weight Linear Polyethylene" Bull. Inst. Chem. Res. vol. 47, No. 3 (1969) p. 209-221.

Collier et al. "Polyethylene: The Past, Present and Future" The American Academy of Orthopaedic Surgeons, 1999 Annual Meeting Scientific Program, available at http://www.aaos.org/wordhtml/anmeet99/sciprog/g.htm. (20 pages).

Dharmastiti et al. "The Wear of Oriented UHMWPE Under Isotropically Rough and Scratched Counterface Test Conditions" Bio-Medical Materials and Engineering. vol. 11 (2001) p. 241-256.

Dijkstra et al. "Cross-linking of Ultra-high Molecular Weight Polyethylene in the Melt by Means of Electron Beam Irradiation" Polymer. vol. 30 (May 1989) p. 866-873.

Dole et al. "Crystallinity and Crosslinking Efficiency in the Irradiation of Polyethylene" Radiat. Phys. Chem. vol. 14 (1979) p. 711-720.

du Plessis et al. "The Improvement of Polyethylene Prostheses Through Radiation Crosslinking" Radiat. Phys. Chem. vol. 9 (1977) p. 647-652.

Ellwanger et al. "Very High Pressure Molding of Ultra High Molecular Weight Polyethylene (UHMWPE)" ANTEC. (1987) p. 572-574.

Gauvin et al., "Investigation of the Radio Frequency Heating Process for UHMWPE" ANTEC. (1987) p. 575-578.

Handlos, V. "Enhanced Crosslinking of Polyethylene" Radiat. Phys. Chem. vol. 14 (1979) p. 721-728.

Jahan et al. "Combined Chemical and Mechanical Effects on Free Radicals in UHMWPE Joints During Implantation" Journal of Biomedical Materials Research. vol. 25 (1991) p. 1005-1017.

Josefsson et al. "Molecular Orientation of Crosslinked Polyethylene" Annual Technical Conference—Society of Plastics Engineers, 58th vol. 2 (2000) p. 1725-1729.

Kang et al. "The Radiation Chemistry of Polyethylene IX. Temperaure Coefficient of Cross-Linking and Other Effects" Journal of the American Chemical Society. vol. 89:9 (1967) p. 1980-1986.

Kanig, G. "Further Electron Microscope Observations on Polyethylene III. Smectic Intermediate State During Melting and Crystallization" Colloid Polym Sci. vol. 269 (1991) p. 1118-1125.

Kato et al. "Structural Changes and Melting Behavior of γ-Irradiated Polyethylene" Japanese Journal of Applied Physics. vol. 20, No. 4. (Apr. 1981) p. 691-697.

Kitamaru et al. "Size and Orientation of Cristallites in Lightly Crosslinked Polyethylene, Crystallized from the Melt Under Uniaxial Compression" Die Makromolekulare Chemie. vol. 175 (1974) p. 255-275.

Kitamaru et al. "Structure and Properties of Lightly Crosslinked Crystalline Polymers Crystallized or Processed Under Molecular Orientation" Journal of Polymer Science: Macromolecular Reviews. vol. 14 (1979) p. 207-264.

Kitamaru et al. "The Properties of Transparent Film Made from Linear Polyethylene by Irradiation Cross-Linking" Properties of Transparent Film. vol. 6, No. 3 (May-Jun. 1973) p. 337-343.

Kitamaru et al. "A Commentary Remark on the Isothermal Crystallization of a Polyethylene Gel from the Stretched Molten State" Bull. Inst. Chem. Res. vol. 46, No. 2 (1968) p. 97-106.

Kurth et al., "Effects of Radiation Sterilization on UHMW-Polyethylene" ANTEC. (1987) p. 1193-1197.

Lewis, G. "Properties of Crosslinked Ultra-High-Molecular Weight Polyethylene" Biomaterials. vol. 22 (2001) p. 371-401.

Lin et al. "Review Structure and Plastic Deformation of Polyethylene" Journal of Materials Science. vol. 29 (1994) p. 294-323.

Matsubara et al. "The Wear Properties of High-Density Polyethylene Irradiated by Gamma Rays" Wear. vol. 10 (1967) p. 214-222.

Meyer, B. "Recent Developments in Radiation Sterilizable Plastics" ANTEC. (1987) p. 1190-1192.

Minkova et al. "Blends of Normal High Density and Ultra-High Molecular Weight Polyethylene, γ Irradiated at a Low Dose" Colloid Polym Sci. vol. 268 (1990) p. 1018-1023.

Minkova, L. "DSC of γ-Irradiated Ultra-High Molecular Weight Polyethylene and High Density Polyethylene of Normal Molecular Weight" Colloid Polym Sci. vol. 266 (1988) p. 6-10.

Muratoglu et al. "A Novel Method of Cross-Linking Ultra-High-Molecular Weight Polyethylene to Improve Wear, Reduce Oxidation, and Retain Mechanical Properties" The Journal of Arthroplasty. vol. 16, No. 2 (2001) p. 149-160.

Nakayama et al. "Structure and Mechanical Properties of Ultra-High Molecular Weight Polyethylene Deformed Near Melting Temperature" Pure & Appl. Chem. vol. 63, No. 12 (1991) p. 1793-1804.

O'Neill et al. "The Distribution of Oxidation Products in Irradiated Ultra-High Molecular Weight Polyethylene" Polymer Degradation and Stability. vol. 49 (1995) p. 239-244.

Oonishi et al. "Comparison of Wear of UHMWPE Sliding Against Metal and Alumina in Total Hip Prostheses—Wear Test and Clinical Results" 3rd World Biomaterials Congress, Transactions. (Apr. 1988) p. 337.

Oonishi et al. "Comparisons of Wear of UHMW Polyethylene Sliding Against Metal and Alumina in Total Hip Prostheses" Bioceramics. vol. 1 (1989) p. 272-277.

Oonishi et al. "Effect of Cross-Linkage by Gamma Radiation in Heavy Doses to Low Wear Polyethylene in Total Hip Prostheses" Journal of Materials Science: Materials in Medicine. vol. 7 (1996) p. 753-763.

Oonishi et al. "Improvement of Polyethylene by Irradiation in Artificial Joints" Radiat. Phys. Chem. vol. 39, No. 6 (1992) p. 495-504.

Oonishi et al. "In Vivo and In Vitro Wear Behaviour on Weightbearing Surfaces of Polyethylene Sockets Improved by Irradiation in Total Hip Prostheses" Surface Modification Technologies V. (1992) p. 101-112.

Oonishi et al. "SEM Observation on the Clinically Used Gamma-Irradiated Reinforced HDP Socket in Total Hip Replacement" Clinical Implant Materials, Advances in Biomaterials, vol. 9 (1990) p. 379-384.

Oonishi et al. "The Optimum Dose of Gamma Radiation-Heavy Doses to Low Wear Polyethylene in Total Hip Prostheses" Journal of Materials Science Materials in Medicine. vol. 8 (1997) p. 11-18.

Oonishi et al. "Wear Resistance of Gamma-Ray Irradiated U.H.M.W. Polyethylene Socket in Total Hip Prosthesis—Wear Test and Long Term Clinical Results" MRS Int'l. Mtg. on Adv. Mats. vol. 1 (1989) p. 351-356.

Oonishi et al. "Wear Resistance of Gamma-Ray Irradiated UHMWPE Socket in Total Hip Prostheses—Wear Test and Long Term Clinical Results" 3rd World Biomaterials Congress, Transactions. (Apr. 1988) p. 588.

Patel, G. "Acceleration of Radiation-Induced Crosslinking in Polyethylene by Diacetylenes" Radiat. Phys. Chem. vol. 14 (1979) p. 729-735.

Premnath et al. "Gamma Sterilization of UHMWPE Articular Implants: an Analysis of the Oxidation Problem" Biomaterials. vol. 17 (1996) p. 1741-1753.

Prins et al. "Biaxial Orientation of Linear Polyethylenes Using the Compressive Deformation Process" Polymer Engineering & Science. vol. 37, No. 2 (Feb. 1997) p. 261-269.

Rimnac et al. "Chemical and Mechanical Degradation of UHMWPE: Report of the Development of an In Vitro Test" Journal of Applied Biomaterials. vol. 5 (1994) p. 17-21.

Rose et al. "Exploratory Investigations on the Structure Dependence of the Wear Resistance of Polyethylene" Wear. vol. 77 (1982) p. 89-104.

Salovey et al. "Irradiation of Ultra High Molecular Weight Polyethylene" Polymer Preprints. vol. 26, No. 1 (1985) p. 118-119.

Salovey, R. "On the Morphology of Crosslinking Polymers" Polymer Letters. vol. 2 (1964) p. 833-834.

Sandford et al. "Shelf Life Prediction of Radiation Sterilized Medical Devices" ANTEC (1987) p. 1201-1204.

Sawatari et al. "Crosslinking Effect of Ultrahigh Molecular Weight Polyethylene-Low Molecular Weight Polyethylene Blend Films Produced by Gelatin/Crystallization From Solutions" Colloid Polym Sci. vol. 269, No. 8 (1991) p. 795-806.

Shen et al. "The Friction and Wear Behavior of Irradiated Very High Molecular Weight Polyethylene" Wear. vol. 30 (1974) p. 349-364.

Shinde et al. "Irradiation of Ultrahigh-Molecular-Weight Polyethylene" Journal of Polymer Science: Polymer Physics Edition. vol. 23 (Feb. 1985) p. 1681-1689.

Streicher, R. "Change in Properties of High Molecular Weight Polyethylenes After Ionizing Irradiation for Sterilization and Modification" Third International Conference on Radiation Processing for Plastics and Rubber (Nov. 1987) (9 pages).

Streicher, R. "Influence of Ionizing Irradiation in Air and Nitrogen for Sterilization of Surgical Grade Polyethylene for Implants" Radiat. Phys. Chem. vol. 31, Nos. 4-6 (1988) p. 693-698.

Streicher, R. "Investigation on Sterilization and Modification of High Molecular Weight Polyethylenes by Ionizing Irradiation" Reprint from beta-gamma Jan. 1989 p. 34-43.

Streicher, R. "Ionizing Irradiation for Sterilization and Modification of High Molecular Weight Polyethylenes" Plastics and Rubber Processing and Applications. vol. 10, (1988) p. 221-229.

Streicher, R. "UHMW—Polyethylen als Werkstoff für artikulierende Komponenten von Gelenkendoprothesen (UHMW Polyethylene Used as a Material for the Articulating Components of Endoprostheses)" Biomed. Technik, vol. 38 (1993) p. 303-313.

Sun et al. "Development of an Accelerated Aging Method for Evaluation of Long-term Irradiation Effects on UHMWPE Implants" Howmedica Inc., Pfizer Hospital Products Group. (1996) p. 969-970.

Sun et al. "Development of Stabilized UHMWPE Implants with Improved Oxidation Resistance Via Crosslinking" American Academy of Orthopaedic Surgeons—Scientific Exhibits, Presented at 63rd Annual Meeting of AAOS. (Feb. 22-26, 1996) p. 179-180.

Waldman et al. "Compressive Stress Relaxation Behavior of Irradiated Ultra-High Molecular Weight Polyethylene at 37° C." Journal of Applied Biomaterials. vol. 5 (1994) p. 333-338.

Wang et al. "Melting of Ultrahigh Molecular Weight Polyethylene" Journal of Applied Polymer Science. vol. 34 (1987) p. 593-599.

Ward, I. "New Developments in the Production of High Modulus and High Strength Flexible Polymers" Progr Colloid Polym Sci. vol. 92 (1993) p. 103-110.

Ward, I. "Recent Developments in Oriented Polymers for Biomedical and Engineering Applications" Macromol. Symp. vol. 195 (2003) p. 293-296.

Williams, J. "Radiation Stability of Polypropylene" ANTEC. (1987) p. 1198-1200.

Wilson et al. "Proton Modification of Ultra High Molecular Weight Polyethylene to Promote Crosslinking for Enhanced Chemical and Physical Properties" Mat. Res. Soc. Symp. Proc. vol. 396 (1996) p. 311-316.

Wong et al. "Molecular Deformation Processes in Gel-Spun Polyethylene Fibres" Journal of Materials Science. vol. 29 (1994) p. 520-526.

Zhao et al. "Effect of Irradiation on Crystallinity and Mechanical Properties of Ultrahigh Molecular Weight Polyethylene" Journal of Applied Polymer Science. vol. 50 (1993) p. 1797-1801.

Zoepfl et al. "Differential Scanning Calorimetry Studies of Irradiated Polyethylene: I. Melting Temperatures and Fusion Endotherms" Journal of Polymer Science: Polymer Chemistry Edition. vol. 22 (1984) p. 2017-2032.

Zoepfl et al. "Differential Scanning Calorimetry Studies of Irradated Polyethylene: II. The Effect of Oxygen" Journal of Polymer Science: Polymer Chemistry Edition. vol. 22 (1984) p. 2033-2045.

Crugnola et al., Ultrahigh Molecular Weight Polyethylene as Used in Articular Prostheses (A Molecular Weight Distribution Study), J. of App. Polymer Science, vol. 20, (1976) pp. 809-812.

Ellis et al., The Use of Ultrahigh Molecular Weight Polyethylene in Articular Prostheses—II. Effects of Fabrication and Gamma Sterilization on Polymer Characteristics, Coatings and Plastics Preprints, vol. 37, No. 2, American Chemical Society, (1977) pp. 280-284.

Greenwald et al., New Polys for Old: Contribution or Caveat?, American Academy of Orthopaedic Surgeons, 69th Annual Meeting (Feb. 13-17, 2002) (6 pages).

Howmedica, Material Properties, Product Quality Control, and Their Relation to UHMWPE Performance, Part Two of a Series on Ultra-High Molecular Weight Polyethylene, (1994) pp. 1-20.

Howmedica, Overview and Fundamentals of UHMWPE, Part One of a Series on Ultra-High Molecular Weight Polyethylene, (1994) pp. 1-8.

Jones et al., Effect of $\gamma$ Irradiation on the Friction and Wear of Ultrahigh Molecular weight Polyethylene, Wear, vol. 70, (1981) pp. 77-92.

Kashiwabara et al., Radiation-Induced Oxidation of Plastics, Radiation Processing of Polymers, Chapter 11, (1992) pp. 221-254.

Kurtz et al., Comparison of the Properties of Annealed Crosslinked (Crossfire™) and Conventional Polyethylene as Hip Bearing Materials, Bulletin—Hospital for Joint Diseases, vol. 61, Nos. 1 & 2, (2002-2003) pp. 17-26.

Narkis et al., Structure and Tensile Behavior of Irradiation—and Peroxide—Crosslinked Polyethylenes, J. Macromol. Sci.—Phys., vol. B 26, No. 1, (1987) pp. 37-58.

Nusbaum et al., The Effects of Radiation Sterilization on the Properties of Ultrahigh Molecular Weight Polyethylene, Journal of Biomedical Materials Research, vol. 13, (1979) pp. 557-576.

Silverman, Radiation-Induced and Chemical Crosslinking: A Brief Comparison, Radiation Processing of Polymers, Chap. 2, (1992) p. 15-22.

Sultan et al., Advances in Crosslinking Technology, Plastics, Rubber and Composites Processing and Applications 21, (1994) pp. 65-73.

Yongxiang et al., Crosslinking of Wire and Cable Insulation Using Electron Accelerators, Radiation Processing of Polymers, Chap. 5, (1992) pp. 71-92.

* cited by examiner

CROSSLINKED POLYMERIC MATERIAL WITH ENHANCED STRENGTH AND PROCESS FOR MANUFACTURING

CROSS REFERENCE TO RELATED APPLICATIONS

This application claims the benefit of U.S. Provisional Application 60/616,811 filed on Oct. 7, 2004, the entire disclosure of which is hereby incorporated by reference.

INTRODUCTION

The invention relates to crosslinked high molecular weight polymeric material and methods for treating the materials to provide enhanced properties. In particular, the invention provides methods and materials for use in preparing polymeric implants with a high degree of wear and oxidation resistance.

Crosslinked ultra high molecular weight polyethylene (UHMWPE) is now widely used in medical implants such as acetabular components for total hip replacements. There remains interest by the orthopedic community to find alternative methods of processing radiation crosslinked UHMWPE to improve mechanical properties while still retaining wear resistance and oxidative stability in the material.

In U.S. Pat. No. 6,168,626, Hyon et al. report enhancement of the mechanical properties of crosslinked UHMWPE by deformation processing at a compression deformable temperature. After deformation processing, the material is cooled while keeping the deformed state. An oriented UHMWPE molded article is obtained that has an orientation of crystal planes in a direction parallel to the compression plane. The compression is carried out using a suitable die or can be done using a hot press machine.

Polymeric materials such as UHMWPE can be crosslinked to provide materials with superior wear properties, for example. The polymeric materials may be chemically crosslinked or preferably crosslinked with irradiation such as γ-irradiation. The action of γ-irradiation on the polymer results in the formation of free radicals within the bulk materials. The free radicals provide sites for reactions to crosslink the molecular chains of the bulk materials. It has become recognized that the presence of free radicals, including any free radicals that survive after subsequent heat treatment, are also susceptible to attack by oxygen to form oxidation products. The formation of such oxidation products generally leads to deterioration of mechanical properties.

To completely remove free radicals and provide polymeric materials of high oxidative stability, it is common to heat treat the crosslinked material above the crystalline melting point of the polymer. This has a tendency to destroy or recombine all of the free radicals in the bulk material. As a result, the crosslinked material is highly resistant to oxidative degradation. However, some desirable mechanical properties are lost during the melting step.

It would be desirable to provide materials such as crosslinked UHMWPE that combine a high level of mechanical properties and a high resistance to oxidative degradation.

SUMMARY

A method for treating a polymeric bulk material comprises heating a cross-linked polymer to a compression deformable temperature. The polymer is in a bulk form characterized by an axial direction. Force is then applied to deform the heated polymer in a direction orthogonal to the axial direction, and the polymer is cooled to a solidification temperature while maintaining the polymer in a deformed state.

In another embodiment, a method for treating crosslinked UHMWPE to make material suitable for use in medical implants comprises heating the UHMWPE to a temperature above about 80° C. and below its melting point, wherein the UHMWPE has been crosslinked with gamma-irradiation and is in the form of a bulk material characterized by an axial direction, a transverse direction orthogonal to the axial direction and an original transverse dimension. Compressive force is then applied to reduce a dimension of the bulk material in the transverse direction, followed by cooling the bulk UHMWPE to a solidification temperature while maintaining compressive force sufficient to prevent the bulk material from returning to its original transverse dimension.

In another embodiment, a UHMWPE pre-form suitable for use in medical implants is prepared by heating a gamma-crosslinked UHMWPE rod characterized by a crystalline melting point and a diameter $d_1$ to a compression deformable temperature; then applying a compression force on the crosslinked UHMWPE to reduce the rod's diameter to $d_2$ less than $d_1$; then cooling the smaller diameter rod of UHMWPE to a solidification temperature while maintaining compression force sufficient to hold the diameter at a diameter of $d_3$, wherein $d_3 < d_1$; and finally stress-relieving the cooled rod by heating it to a temperature at which the rod expands to a diameter $d_4$, wherein $d_4 > d_3$.

Products of the process include a compression deformed crosslinked polymeric material suitable for use as bearing components such as acetabular cups in medical implants such as those used in hip replacements. In a preferred embodiment, ultrahigh molecular weight polyethylene is provided that has a combination of a high tensile strength at break and a high resistance to oxidative degradation.

BRIEF DESCRIPTION OF THE DRAWINGS

The present invention will become more fully understood from the detailed description and the accompanying drawings, wherein.

DESCRIPTION

Figure 1:
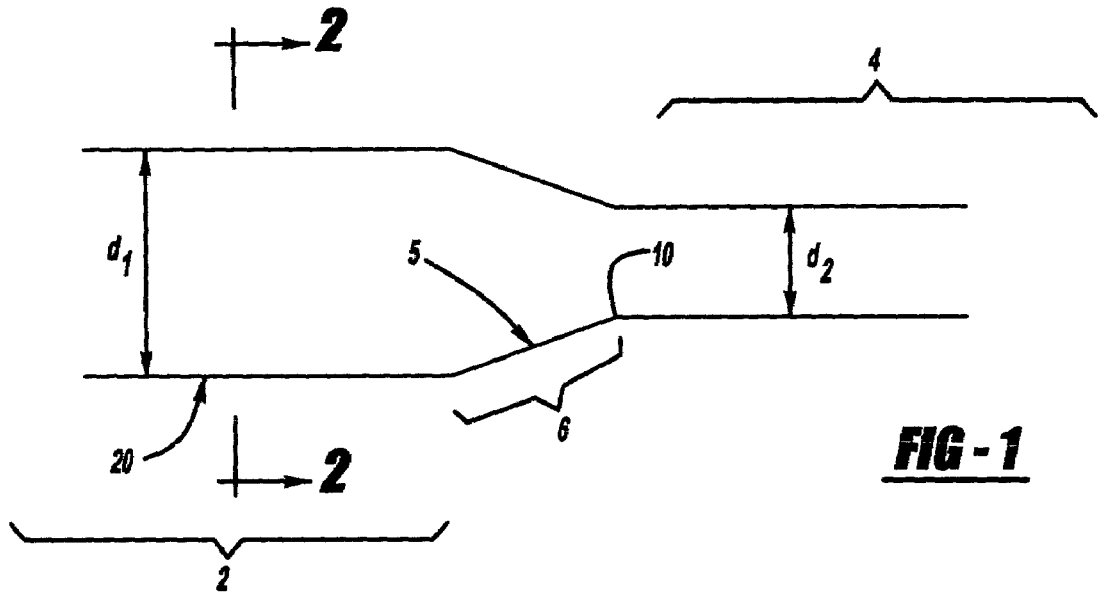
FIG. 1 illustrates the geometry of an extrusion process.
Figure 2A:
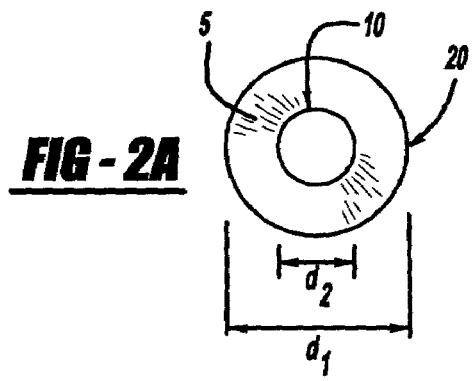
FIG. 2 shows various embodiments of extrusion apparatus and dies.
Figure 2B:
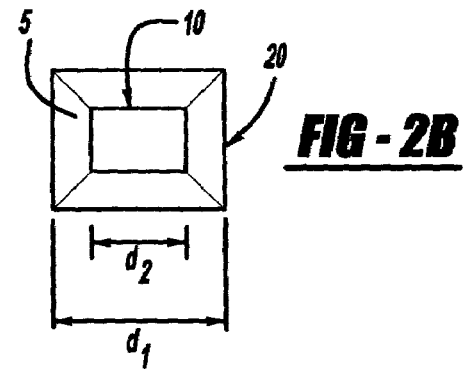
Figure 2C:
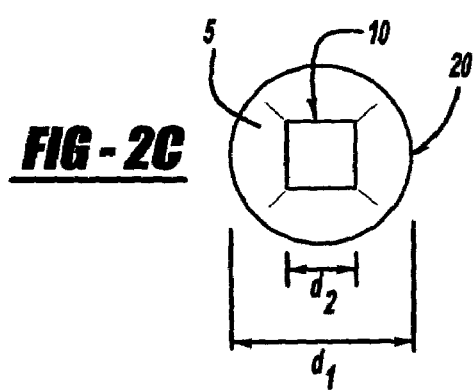
Figure 2D:
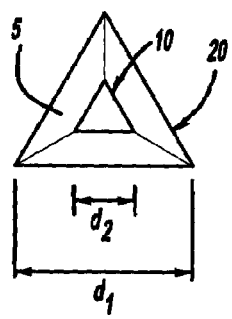
Figure 2E:
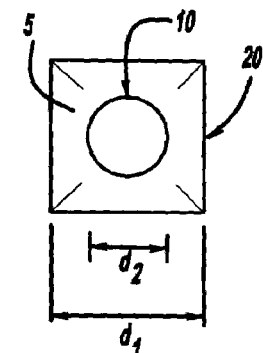

The headings (such as "Introduction" and "Summary,") used herein are intended only for general organization of topics within the disclosure of the invention, and are not intended to limit the disclosure of the invention or any aspect thereof. In particular, subject matter disclosed in the "Introduction" may include aspects of technology within the scope of the invention, and may not constitute a recitation of prior art. Subject matter disclosed in the "Summary" is not an exhaustive or complete disclosure of the entire scope of the invention or any embodiments thereof. Similarly, subpart headings in the Description are given for convenience of the reader, and are not a representation that information on the topic is to be found exclusively at the heading.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations of the stated features. Specific Examples are provided for illustrative purposes of how to make, use and practice the compositions and methods of this invention and, unless explicitly stated otherwise, are not intended to be a representation that given embodiments of this invention have, or have not, been made or tested.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the word "include," and its variants, is intended to be non-limiting, such that recitation of items in a list is not to the exclusion of other like items that may also be useful in the materials, compositions, devices, and methods of this invention.

In one embodiment, the invention provides a method for treating a polymeric bulk material comprising heating a crosslinked polymer to a compression deformable temperature, applying force to deform the heated polymer, and cooling the polymer to a solidification temperature while maintaining the polymer in a deformed state. The crosslinked polymer is in a bulk form characterized by an axial direction; force is applied to deform the heated polymer in a direction orthogonal to the axial direction. Among other desirable physical properties, the polymeric bulk material as treated by the above method exhibits enhanced strength in the axial direction of the bulk material. When the bulk material is UHMWPE, the method is especially suitable for providing a medical implant containing bearing components made out of the UHMWPE.

In another embodiment, the invention provides a method for treating crosslinked UHMWPE for making material suitable for use in a medical implant. The method involves heating UHMWPE to a temperature above about 80° C. and below its melting point, where the UHMWPE has been crosslinked with γ-irradiation. The UHMWPE is in the form of a bulk material characterized by an axial direction, a transverse direction orthogonal to the axial direction, and an original dimension. Compressive force is then applied on the bulk material in the transverse direction to the reduce a dimension of the bulk material in that direction. Then the bulk UHMWPE is cooled to a solidification temperature. In one embodiment, force is applied during the cooling sufficient to prevent the bulk material from returning to its original dimension. In various embodiments, compressive force is applied by ram extruding the bulk material through a reducing die, for instance through a circular die, with a diametral compression or draw ratio greater than 1.

In various embodiments, compressive force is maintained on the cooling UHMWPE by extruding the heated crosslinked bulk material into a chamber of sufficient size and shape to hold the bulk material at a dimension in the transverse direction less than original radial dimension In particular embodiments, the invention provides a method for preparing a preform made of UHMWPE suitable for use in medical implants. The method comprises heating a γ-irradiation crosslinked UHMWPE rod characterized by a crystalline melting point and a diameter $d_1$ to a compression deformable temperature. Thereafter, compression force is applied on the crosslinked UHMWPE to decrease the diameter to $d_2$, wherein $d_2$ is less than $d_1$. The reduced diameter rod of UHMWPE is optionally cooled to a solidification temperature while maintaining compression force to keep the diameter at a value of $d_3$, wherein $d_3$ is less than $d_1$. In a subsequent step, the cooled rod is stress relieved by heating to a temperature at which the rod expands to a diameter $d_4$, wherein $d_4$ is greater than $d_3$. In various embodiments, the method involves extruding the rod through a reducing die into a cooling chamber to reduce the diameter from $d_1$ to $d_2$. The compression deformable temperature is preferably less than the melting point and greater than a temperature equal to the melting point minus 50° C. In a preferred embodiment, the compression deformable temperature is from about 100° C. to about 135° C. Preferably, the UHMWPE rod has been crosslinked with γ-irradiation at a dose from 0.1 to 10 Mrad. Methods are also provided for making a bearing component for a medical implant from UHMWPE treated according to the method above, as well as implants comprising a UHMWPE machined from a preform made according to the above methods.

In one aspect, the invention provides a γ-crosslinked UHMWPE in the form of an elongate material, such as a cylinder, characterized by an axial direction. The tensile strength in the axial or longitudinal direction is greater than 50 MPa and preferably greater than 60 MPa. In preferred embodiments, bearing components comprise UHMWPE machined or formed from such a γ-crosslinked UHMWPE. Medical implants contain the bearing components.

In another aspect, the invention provides a γ-crosslinked UHMWPE having a detectable concentration level of free radicals, but nevertheless stable to oxidation as measured by standard tests. For example, in a non-limiting example, the concentration of free radicals in the UHMWPE is above about $0.06 \times 10^{15}$ spins/g and below about $3 \times 10^{15}$ spins/g. Preferably, the free radical concentration is $1.5 \times 10^{15}$ spins/g or less. In a preferred embodiment, there is no detectable increase in the carbonyl IR absorption band during exposure to oxygen at 5 atmospheres for four weeks at 70° C. The crosslinked UHMWPE is advantageously provided in the form of a cylindrical rod having a diameter of about 2 to 4 inches and preferably about 3 inches. Bearing components are provided by machining the components from the crosslinked UHMWPE, and medical implants are provided that contain the bearing components.

In a further aspect, an anisotropic crosslinked UHMWPE is provided in the form of a bulk material characterized by an axial direction and a transverse direction orthogonal to the axial direction. In various embodiments, the anisotropy is characterized in that the tensile strength in the axial direction is 20% or more greater than the tensile strength in the radial direction, and attains the value of at least 50 MPa, preferably at least 60 MPa.

In a further aspect, a method for solid state deformation processing of γ-irradiated crosslinked UHMWPE comprises deforming the UHMWPE by extruding it at a temperature below its melt transition or crystalline melting point. In subsequent steps, the extruded UHMWPE is cooled to a temperature below its solidification temperature, optionally while maintaining the extruded rod in a deformed state.

In other embodiments, a compression deformed crosslinked UHMWPE having a tensile strength at break of more than 50 MPa is provided by treating UHMWPE according to the methods. In preferred embodiments, the material is also resistant to oxidative degradation, characterized by an oxidation index less than 0.5 after exposure to 5 atm of oxygen at 70° C. for 4 days, in spite of the material having a detectable free radical concentration above $0.06 \times 10^{15}$ spins/g.

In another aspect, the invention provides a method for making a medical implant containing a bearing component made of UHMWPE. The method includes the steps of radiation crosslinking a UHMWPE in the form of a bulk material, preheating the crosslinked UHMWPE to a temperature above 80° C. and below its melting point, then solid state extruding the preheated UHMWPE to a diametral compression ratio of greater than 1, cooling the extruded UHMWPE to a solidification temperature below 30° C. while maintaining diametral compression, annealing the cooled UHMWPE at a temperature below the melting point for a time sufficient for the rod to increase in diameter in response to the annealing, and machining the bearing component from the annealed UHMWPE. The UHMWPE is optionally sterilized after machining the bearing component. Sterilizing is preferably performed by non-irradiative means such as exposure to gases such as ethylene oxide.

In various embodiments, implants are manufactured using preformed polymeric compositions having the structures described herein and made by the methods described herein. Non-limiting examples of implants include hip joints, knee joints, ankle joints, elbow joints, shoulder joints, spine, temporo-mandibular joints, and finger joints. In hip joints, for example, the preformed polymeric composition can be used to make the acetabular cup or the insert or liner of the cup. In the knee joints, the compositions can be made used to make the tibial plateau, the patellar button, and trunnion or other bearing components depending on the design of the joints. In the ankle joint, the compositions can be used to make the talar surface and other bearing components. In the elbow joint, the compositions can be used to make the radio-numeral or ulno-humeral joint and other bearing components. In the shoulder joint, the compositions can be used to make the glenero-humeral articulation and other bearing components. In the spine, intervertebral disc replacements and facet joint replacements may be made from the compositions.

In various embodiments, the bearing components are made from the polymeric compositions by known methods such as by machining and are incorporated into implants by conventional means.

Polymers

For implants, preferred polymers include those that are wear resistant, have chemical resistance, resist oxidation, and are compatible with physiological structures. In various embodiments, the polymers are polyesters, polymethylmethacrylate, nylons or polyamides, polycarbonates, and polyhydrocarbons such as polyethylene and polypropylene. High molecular weight and ultra high molecular weight polymers are preferred in various embodiments. Non-limiting examples include high molecular weight polyethylene, ultra high molecular weight polyethylene (UHMWPE), and ultra high molecular weight polypropylene. In various embodiments, the polymers have molecular ranges from approximate molecular weight range in the range from about 400,000 to about 10,000,000.

UHMWPE is used in joint replacements because it possesses a low co-efficient of friction, high wear resistance, and compatibility with body tissue. UHMWPE is available commercially as bar stock or blocks that have been compression molded or ram extruded. Commercial examples include the GUR series from Hoechst. A number of grades are commercially available having molecular weights in the preferred range described above.

Crosslinking

According to various embodiments of the invention, a crosslinked polymeric bulk material is further processed in a series of heating, deforming, cooling, and machining steps. The polymeric bulk material can be crosslinked by a variety of chemical and radiation methods.

In various embodiments, chemical crosslinking is accomplished by combining a polymeric material with a crosslinking chemical and subjecting the mixture to temperature sufficient to cause crosslinking to occur. In various embodiments, the chemical crosslinking is accomplished by molding a polymeric material containing the crosslinking chemical. The molding temperature is the temperature at which the polymer is molded. In various embodiments, the molding temperature is at or above the melting temperature of the polymer.

If the crosslinking chemical has a long half-life at the molding temperature, it will decompose slowly, and the resulting free radicals can diffuse in the polymer to form a homogeneous crosslinked network at the molding temperature. Thus, the molding temperature is also preferably high enough to allow the flow of the polymer to occur to distribute or diffuse the crosslinking chemical and the resulting free radicals to form the homogeneous network. For UHMWPE, a preferred molding temperature is between about 130° C. and 220° C. with a molding time of about 1 to 3 hours. In a non-limiting embodiment, the molding temperature and time are 170° C. and 2 hours, respectively.

The crosslinking chemical may be any chemical that decomposes at the molding temperature to form highly reactive intermediates, such as free radicals, that react with the polymers to form a crosslinked network. Examples of free radical generating chemicals include peroxides, peresters, azo compounds, disulfides, dimethacrylates, tetrazenes, and divinylbenzene. Examples of azo compounds are: azobis-isobutyronitrile, azobis-isobutyronitrile, and dimethylazodi-isobutyrate. Examples of peresters are t-butyl peracetate and t-butyl perbenzoate.

Preferably the polymer is crosslinked by treating it with an organic peroxide. Suitable peroxides include 2,5-dimethyl-2, 5-bis(tert-butylperoxy)-3-hexyne (Lupersol 130, Atochem Inc., Philadelphia, Pa.); 2,5-dimethyl-2,5-di-(t-butylperoxy)-hexane; t-butyl α-cumyl peroxide; di-butyl peroxide; t-butyl hydroperoxide; benzoyl peroxide; dichlorobenzoyl peroxide; dicumyl peroxide; di-tertiary butyl peroxide; 2,5-dimethyl-2, 5-di(peroxy benzoate)hexyne-3; 1,3-bis(t-butyl peroxy isopropyl) benzene; lauroyl peroxide; di-t-amyl peroxide; 1,1-di-(t-butylperoxy) cyclohexane; 2,2-di-(t-butylperoxy) butane; and 2,2-di-(t-amylperoxy) propane. A preferred peroxide is 2,5-dimethyl-2,5-bis(tert-butylperoxy)-3-hexyne. The preferred peroxides have a half-life of between 2 minutes to 1 hour; and more preferably, the half-life is between 5 minutes to 50 minutes at the molding temperature.

Generally, between 0.2 to 5.0 wt % of peroxide is used; more preferably, the range is between 0.5 to 3.0 wt % of peroxide; and most preferably, the range is between 0.6 to 2 wt %.

The peroxide can be dissolved in an inert solvent before being added to the polymer powder. The inert solvent preferably evaporates before the polymer is molded. Examples of such inert solvents are alcohol and acetone.

For convenience, the reaction between the polymer and the crosslinking chemical, such as peroxide, can generally be carried out at molding pressures. Generally, the reactants are incubated at molding temperature, between 1 to 3 hours, and more preferably, for about 2 hours.

The reaction mixture is preferably slowly heated to achieve the molding temperature. After the incubation period, the crosslinked polymer is preferably slowly cooled down to room temperature. For example, the polymer may be left at room temperature and allowed to cool on its own. Slow cooling allows the formation of a stable crystalline structure.

The reaction parameters for crosslinking polymers with peroxide, and the choices of peroxides, can be determined by one skilled in the art. For example, a wide variety of peroxides are available for reaction with polyolefins, and investigations of their relative efficiencies have been reported. Differences in decomposition rates are perhaps the main factor in selecting a particular peroxide for an intended application.

Peroxide crosslinking of UHMWPE has also been reported. UHMWPE can be crosslinked in the melt at 180° C. by means of 2,5-dimethyl-2,5-di-(tert-butylperoxy)-hexyne-3.

In various embodiments, crosslinking is accomplished by exposing a polymeric bulk material to irradiation. Non-limiting examples of irradiation for crosslinking the polymers include electron beam, x-ray, and gamma-irradiation. In various embodiments, gamma irradiation is preferred because the radiation readily penetrates the bulk material. Electron beams can also be used to irradiate the bulk material. With e-beam radiation, the penetration depth depends on the energy of the electron beam, as is well known in the art.

For gamma (γ) irradiation, the polymeric bulk material is irradiated in a solid state at a dose of about 0.01 to 100 Mrad (0.1 to 1000 kGy), preferably from 0.01 to 10 MRad, using methods known in the art, such as exposure to gamma emissions from an isotope such as $^{60}$Co. In various embodiments, gamma irradiation is carried out at a dose of 0.01 to 6, preferably about 1.5 to 6 Mrad. In a non-limiting embodiment, irradiation is to a dose of approximately 5 MRad.

Irradiation of the polymeric bulk material is usually accomplished in an inert atmosphere or vacuum. For example, the polymeric bulk material may be packaged in an oxygen impermeable package during the irradiation step. Inert gases, such as nitrogen, argon, and helium may also be used. When vacuum is used, the packaged material may be subjected to one or more cycles of flushing with an inert gas and applying the vacuum to eliminate oxygen from the package. Examples of package materials include metal foil pouches such as aluminum or Mylar® coating packaging foil, which are available commercially for heat sealed vacuum packaging. Irradiating the polymeric bulk material in an inert atmosphere reduces the effect of oxidation and the accompanying chain scission reactions that can occur during irradiation. Oxidation caused by oxygen present in the atmosphere present in the irradiation is generally limited to the surface of the polymeric material. In general, low levels of surface oxidation can be tolerated, as the oxidized surface can be removed during subsequent machining.

Irradiation such as γ-irradiation can be carried out on polymeric material at specialized installations possessing suitable irradiation equipment. When the irradiation is carried out at a location other than the one in which the further heating, compressing, cooling, and machining operations are to be carried out, the irradiated bulk material is conveniently left in the oxygen impermeable packaging during shipment to the site for further operations.

Bulk Form of the Materials

The crosslinked polymer is provided in a bulk form characterized by an axial direction and a transverse direction orthogonal or perpendicular to the axial direction. In subsequent processing steps, deformation pressure is applied on the crosslinked bulk material to reduce a dimension in the transverse direction.

The axial direction is also the direction in which high tensile strength is developed, as described further below. In this aspect, the axial direction of the bulk material is the direction perpendicular to the application of the deformation force that leads to development of high tensile strength in the axial direction. In this way, application of deformation pressure or force orthogonal to the axial direction creates an anisotropic material, characterized by higher tensile strength in the axial than in the transverse direction.

The axial direction of the bulk material also defines the preferred direction in which implant bearing components such as acetabular cups are to be machined. That is, bearing components are preferably made or machined from the treated bulk polymer in an orientation where the high tensile strength axis of the polymer corresponds to the load bearing axis or direction of the bearing component of the implant in vivo.

In an exemplary embodiment, the bulk material is in the form of a rod or cylinder having a circular cross section. The axial direction is parallel to the main axis of the cylinder, while the transverse direction is at right angles to the axial direction. In other words, the existence of the axial direction defines an orthogonal direction referred to as "transverse" in this application. When the cross section of the bulk material is isotropic as in the case of a cylinder, the transverse direction can be described as "radial", and the transverse axis as a radial axis. The main axis of the bulk material can also be called the longitudinal axis. As used here, the longitudinal axis is parallel to the axial direction.

In the non-limiting case of a rod or cylinder, a cross section of the bulk material perpendicular to the axial direction or longitudinal axis is a circle. Other bulk materials characterized by an axial direction may be used that have other perpendicular cross sections. In a non-limiting example, a square cylinder can be provided that has a square cross section perpendicular to the axial direction. Other bulk materials characterized by an axial direction can have rectangular, polygonal, star, lobed, and other cross sections perpendicular to the axial direction.

In various embodiments, the axial direction of the bulk polymeric material is elongated compared to the orthogonal or radial direction. For example, in the case of UHMWPE, a commercially available bulk material is a cylinder approximately 3 inches in diameter and 14 inches in length. The length corresponds to the axial direction and the diameter corresponds to the radial direction. As described below, bearing components for implants are preferably machined from billets cut in the axial direction. For efficiency in manufacturing it is convenient to produce a number of bearing components from a single bulk material treated by the methods of the invention. For this reason, the bulk material is usually to be extended in an axial direction so as to be able to cut a plurality of billets from the material for use in further machining of the bearing components.

As described above, bulk material characterized by an axial direction is further characterized as having a variety of cross sectional areas perpendicular to the axial direction. In various embodiments, the dimensions of the cross sectional areas perpendicular to the axial direction are more or less constant along the axial direction from the beginning to the end or from the top to the bottom of the bulk material. In various other embodiments, bulk materials may be provided to have cross sectional areas that vary along the length or axial direction of the bulk material. In the case where the cross sectional area of the bulk material is constant along the axial direction of the bulk material, compressive force applied as described below will generally be applied to the bulk material in a direction perpendicular to the axial direction. In the case where the cross sectional area varies along the axial direction of the bulk material, compressive force applied to the bulk material may have a component in the axial direction due to the geometry of the bulk material. However, in all cases at least a component of the compressive force will be applied on the bulk material in a direction orthogonal to the axial direction.

Pre-Heating

Before further processing, the crosslinked polymer is heated to a compression deformable temperature. The compression deformable temperature is temperature at which the polymeric bulk material softens and can flow under the application of a compressive source to change dimension in the direction the compressive force is applied. For UHMWPE and other polymeric materials, the compression deformable temperature is concretely from about the melting point minus 50° C. to the melting point plus 80° C.

In various embodiments, the compression deformable temperature is below the melting point of the polymeric material. Examples of the compression deformable temperature include from the melting point to 10° C. below the melting point, from the melting point to 20° C. below the melting point, from the melting point to 30° C. below the melting point, and from the melting point to 40° C. below the melting point. For UHMWPE, the compression deformable temperature is above 80° C., or from about 86° C. to about 136° C., since the melting temperature of the UHMWPE is about 136° C. to 139° C. In various embodiments, the compression deformable temperature of UHMWPE lies from about 90° C. to 135° C., preferably about 100° C. to 130° C. A preferred temperature is 125-135° C., or 130° C.±5° C.

In various embodiments, the crosslinked material is heated to a compression deformable temperature above the melting point of the polymer. For UHMWPE and other polymeric materials, such a compression deformable temperature is from just above the melting point to a temperature about 80° C. higher than the melting point. For example, UHMWPE can be heated to a temperature of 160° C. to 220° C. or 180° C. to 200° C.

In various embodiments, it is preferred to heat the bulk polymeric material to a compression deformation temperature close to but not higher than the melting point. In various embodiments, the compression deformable temperature is between the melting point and a temperature 20° C. lower than the melting point, or between the melting point and a temperature 10° C. lower than the melting point.

The crosslinked bulk material can be heated to a compression deformable temperature in a deformation chamber as illustrated in the figures, or it can be preheated in an oven to the compression deformable temperature. In various embodiments, the bulk material is heated to a temperature just below the melting point, such as the melting point minus 5° or the melting point minus 10° and placed in a heated deformation chamber. The deformation chamber preferably maintains a compression deformable temperature. If desired, the deformation chamber can be heated or thermostatted to maintain a constant temperature. Alternatively, the deformation chamber is not itself heated but has sufficient insulating properties to maintain the bulk material at a compression deformable temperature during the course of extrusion through the reducing die described below. In various embodiments, the temperature of the deformation chamber is held at several degrees below the melting temperature to avoid melting.

Deformation

When the crosslinked bulk material is at a compression deformable temperature, deforming pressure is applied to the bulk material in a direction orthogonal to the axial direction. The application of the orthogonal force results in material flow of the heated bulk material. As a result, a dimension of the bulk material in the transverse direction at which force is applied is diminished compared to the original dimension. As discussed above, compression force is applied so that least one component of the force is orthogonal to the axial direction of the bulk material. For cylindrical rods and other bulk materials that have a constant cross section along the axial direction of the bulk material, the compression force is applied in a direction perpendicular to the axial direction.

Any suitable methods may be used to apply the compression force in a direction orthogonal to the axial direction. Non-limiting examples include rollers, clamps, and equivalent means.

Extrusion

In various embodiments, deforming force is applied in the directional orthogonal to the axial direction of the bulk material by extruding the bulk material through a reducing die. Pressure exerted on the bulk material in a direction orthogonal to the axial direction during extrusion causes the dimension of the bulk material to be reduced compared to the original dimension of the bulk material. In other words, the diameter or other transverse dimension of the bulk material after extrusion is less than the dimension before extrusion.

The relative reduction in the dimension of the bulk material in the transverse directions can be expressed as a ratio of the original dimension $d_1$ to the reduced dimension $d_2$. Depending on the method of reducing the dimension by applying compressive force, the numeric value of the ratio $d_1/d_2$ can be referred to as a draw ratio or a diametral compression. For extrusion, it is common practice to refer to a draw ratio; unless stated otherwise from context, the term draw ratio will be used here to refer to all geometries.

It is to be understood that the transverse direction (the direction orthogonal to the axial direction) in which deformation pressure or force is applied itself contains two axes that can be drawn at right angles to the longitudinal axis. In various embodiments, the bulk material can be deformed by a different amount along the two transverse axes, and a draw ratio can be defined for both axes. The orientation of the transverse axes is arbitrary; if needed for analysis, the axes can be selected to simplify the geometry of the applied forces. When the cross section of the bulk material is isotropic, equal deformation force can be applied in all transverse directions. In this non-limiting case, the dimension $d_2$ corresponds to the radius or diameter of the extruded material, and the draw ratio is the fraction defined by dividing $d_1$ by $d_2$.

In various embodiments, the draw ratio is 1.1 or higher, and less than about 3. In various embodiments, the draw ratio is 1.2 or higher, and is preferably about 1.2 to 1.8. It is about 1.5 in a non-limiting example. At high levels of reduction, a point is reached at which the strain introduced is too great and the properties of the crosslinked polymeric materials deteriorate. Accordingly, in various embodiments the draw ratio is 2.5 or less, and preferably about 2.0 or less. In a preferred embodiment, the compressive force is applied more or less isotropically around the bulk material in a direction transverse to a longitudinal axis. Accordingly, the reduction in dimension will usually apply in all transverse directions. To illustrate, a circular cross section remains round but is reduced in diameter, while a polygonal cross section such as a square or rectangle is reduced on all sides.

The geometry of extrusion through a reducing die is illustrated in schematic form in FIGS. 1 and 2. A reducing die 6 is disposed between a deformation chamber 2 and a cooling chamber 4. As shown, the reducing 6 die serves to reduce the diameter or dimension of the extruded rod from an original dimension $d_1$ to an extruded dimension $d_2$. As the crosslinked heated bulk material passes from the deformation chamber through the reducing die 6, the material flows by the die wall 5 that leads to a constriction 10 having the diameter $d_2$ of the cooling chamber 4.

Various geometries of the reducing die are illustrated in non-limiting form in FIG. 2. FIGS. 2a to 2e show the relative configuration of the deformation chamber wall 20 and the cooling chamber wall 10. The die wall 5 is seen to connect the cooling deformation chamber to the cooling chamber. In FIG. 2a, the cross section of both the deformation chamber 2 and cooling chamber 4 are circular, with dimensions $d_1$ and $d_2$ corresponding to their respective diameters. In FIG. 2b, the deformation chamber is square or rectangular characterized by a dimension d1 that can be arbitrarily taken along a diagonal or along a side. In FIG. 2b, the cooling chamber 4 is also rectangular but having lower dimension $d_2$. FIGS. 2c through 2e illustrate other combinations of circular, square, and triangular deformations and cooling chambers connected by reducing dies 6 having a die wall 5, and are offered by way of non-limiting example.

As noted above, the bulk material in the deformation chamber 2 is held at a compression deformable temperature. At such a temperature, the material can flow in response to pressure exerted on the material. When the compression deformable temperature is below the melting point, the material undergoes a solid state flow through the reducing die 6. Pressure or force applied to the end of the bar by the ram is translated by the die into compressive force that reduces the dimension of the bulk material in the transverse direction. Conveniently, the diameter of the bulk material to be extruded matches relatively closely the diameter or dimension $d_1$ of the deformation chamber illustrated in FIG. 1.

Cooling

In various embodiments, an extruded UHMWPE rod or other crosslinked polymeric material in a bulk form characterized by an axial direction is cooled before further processing. Alternatively, the extruded bulk material can be directly processed by the stress relief step described below. In a non-limiting embodiment, the rod or other bulk material characterized by an axial direction is cooled to a solidification temperature in a cooling chamber or other means while pressure is maintained sufficient to keep the dimension of the extruded bulk material below the original dimension of the crosslinked bulk material. In the extrusion or other compressive force embodiments, the pressure required to maintain the dimension lower than the original dimension may be more or less pressure than required to originally change the shape of the polymer, such as through extrusion. As noted, the bulk material such as extruded UHMWPE is held in a cooling chamber or similar device for a sufficient time to reach a temperature at which the bulk material no longer has a tendency to increase in dimension upon removal of the pressure. This temperature is designated as the solidification temperature; for UHMWPE the solidification temperature is reached when a thermostat embedded in the cooling wall (about 1 mm from the inside wall surface) reads about 30° C. The solidification temperature is not a phase change temperature such as a melting or freezing. It is also to be noted that a material such as UHMWPE can be cooled to the solidification temperature independently of whether the material was heated above or below the melting point in a previous processing step.

In various embodiments, after extrusion or other application of deforming force in a direction orthogonal to the axial direction of the crosslinked polymeric bulk material, the compressive deforming force is maintained on the bulk material until the bulk material cools to the solidification temperature. Such a maintenance of compressive force is conveniently provided in the reducing die embodiment illustrated in FIGS. 1 and 2. After extrusion through the reducing die 6, the bulk material is held in the cooling chamber 4. In the embodiment shown in the Figures, the cooling chamber is of such a size and shape as to hold the extruded bulk material at a dimension or diameter $d_3$, which is less than the original dimension $d_1$ of the bulk material and is conveniently about the same as the extruded dimension $d_2$ in a non-limiting example. The crosslinked material has a tendency to return to its original dimension by expanding when the temperature is above the solidification temperature. The expansion force of the bulk material is counteracted by the walls of the cooling chamber, with the result that compressive force is maintained on the bulk material while it cools. In various embodiments, the cooling chamber is provided with cooling means such as cooling jackets or coils to remove heat from the cooling chamber and the extruded polymer bulk material.

Referring to the figures for illustration, as the polymeric extruded bulk material cools in the cooling chamber, a temperature is reached at which the material no longer has a tendency to expand or revert to its original dimension $d_1$. At this temperature, called the solidification temperature, the bulk material no longer exerts pressure on the walls of the cooling chamber and can be removed. In preferred embodiments, the material is cooled to about 30° C., as measured by thermostats in the walls of the chamber, before removal.

The temperatures of the deformation chamber and the cooling chamber can be measured by conventional means, such as by thermocouples embedded into the walls of the respective chambers. For example, it has been found that when a thermocouple in the wall of the cooling chamber indicates a temperature of 30° C., an extruded bulk material made of UHMWPE has reached a bulk temperature below a solidification temperature at which the material loses it tendency to expand. The temperature as measured with, for example, a thermocouple embedded in the wall of the cooling chamber does not necessarily represent a bulk or equilibrium temperature of the material in the cooling chamber. An appropriate rate of cooling may be provided in the cooling chamber by use of heat exchange fluids such as water or water glycol mixture, and the bulk material held in the cooling chamber for a time and until a temperature is reached at which it is observed that removal of the bulk material from the chamber does not result in significant increase in diameter. Thus, in various embodiments, cooling to a solidification temperature of, for example, 90° F. or 30° C. means leaving the extruded bulk material in the cooling chamber until the thermocouple embedded in the walls of the cooling chamber reads 90° F. or 30° C. As noted, it has been found that such a cooling period suffices for removal of the bulk material, even though the bulk equilibrium temperature of the interior of the bulk material could be higher than the measured temperature.

In various embodiments, the extruded bulk material is held in the cooling chamber for an additional period of time, such as 10 minutes, after the embedded thermocouple reads 90° F. or 30° C. The additional cooling period can enable the cooled material to be more easily removed from the cooling chamber. In one embodiment, when the thermocouple reaches a reading of 30° C., a programmable logic controller (plc) starts a timer that in turns gives a signal when the desired time has passed. At that time an operator can remove the compression deformed crosslinked material from the chamber, or rams or other suitable devices can be actuated to effect removal.

Sacrificial Puck

Figure 3A:
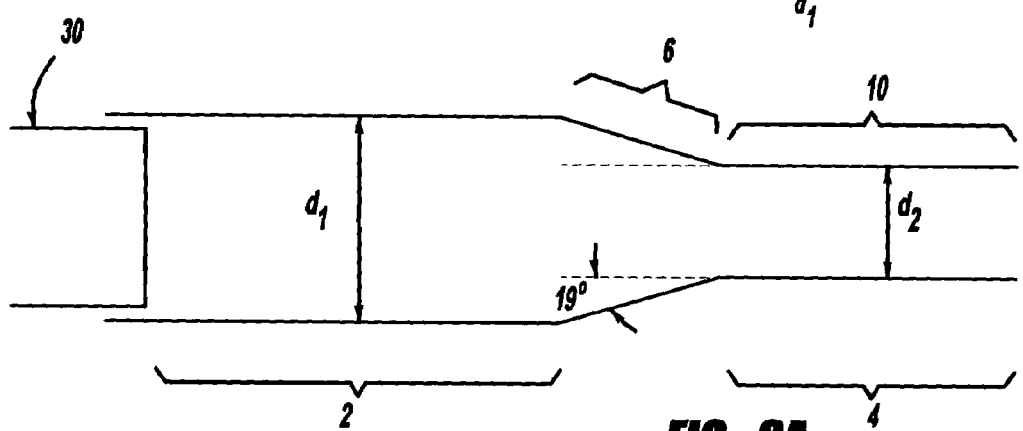
FIG. 3 illustrates an embodiment of an extrusion process.
Figure 3B:
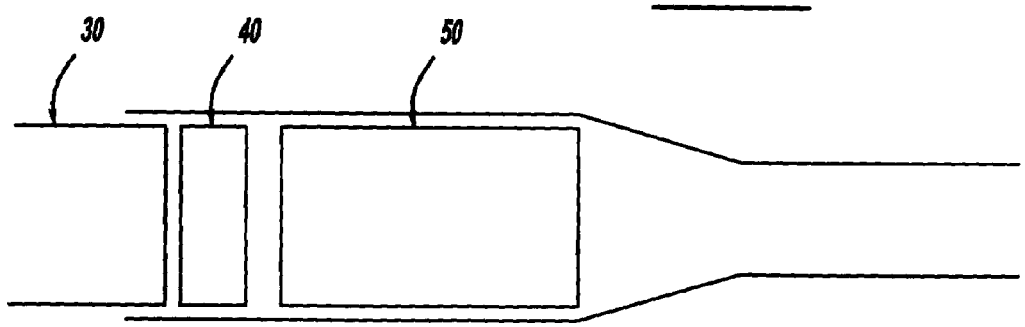
Figure 3C:
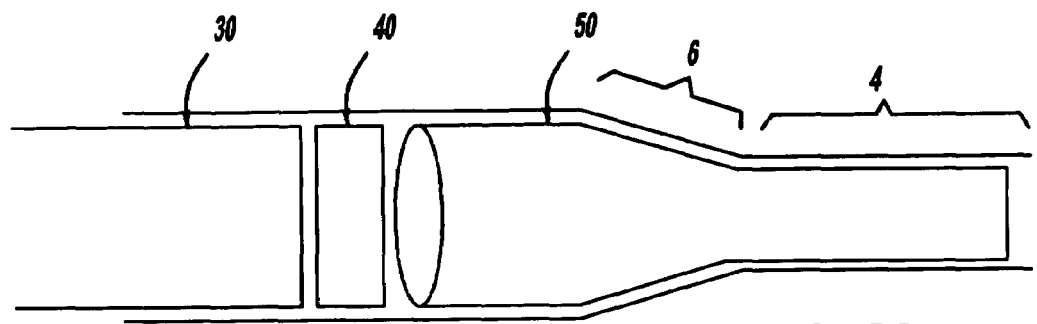
Figure 3D:
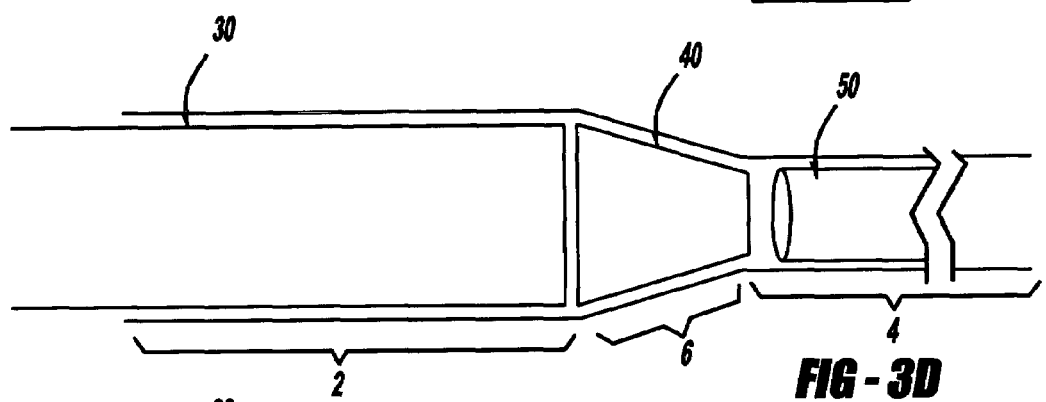
Figure 3E:
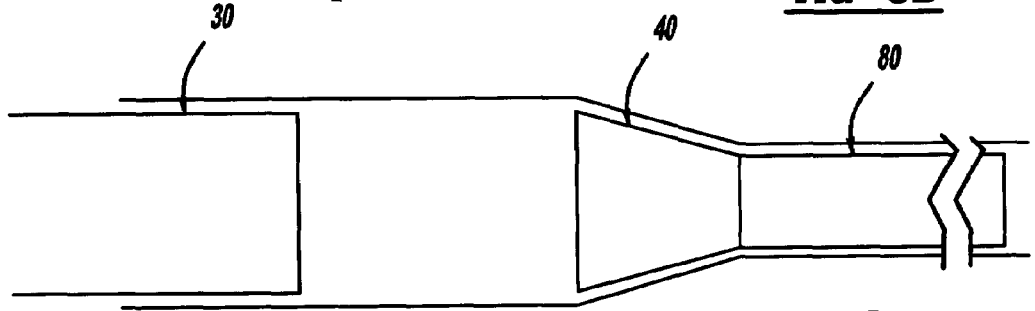
Figure 3F:
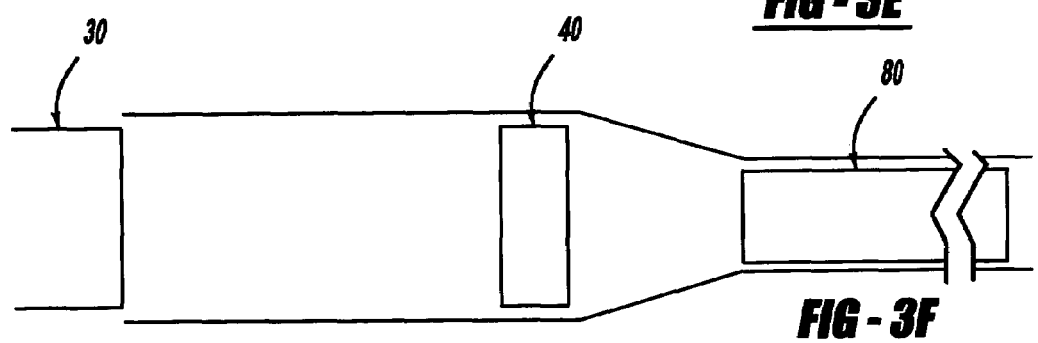

In a preferred embodiment, a so-called sacrificial puck is used to improve the efficiency of the extrusion process. In referring to FIG. 3, a ram 30 is provided in a retracted position with respect to the deformation chamber 2. FIG. 3b shows the ram 30 retracted and the deformation chamber 2 filled with a rod-like bulk material 50 and a sacrificial puck 40. The sacrificial puck 40 is made of a crosslinked polymer, which may be the same as the crosslinked polymer of the bulk material 50. It is preferably of approximately the same cross-sectional shape and area as the bulk material 50 to be extruded. In FIG. 3c, the ram 30 is shown pushing on the sacrificial puck 40, which in turn pushes on the bulk material 50 to move the bulk material 50 through the reducing die 6 into the cooling chamber 4. FIG. 3d shows the situation at the end of the stroke of the ram 30. The bulk material 50 is sitting completely in the cooling chamber 4, while the sacrificial puck 30 occupies the reducing die 6. Upon retraction of the ram 30 as shown in FIG. 3e, the sacrificial puck 40 tends to return to its original dimension because it is not being cooled in the cooling chamber as the bulk material 50 is. As a result, the sacrificial puck tends to extricate itself from the reducing die as shown in FIG. 3f. The sacrificial puck 40 can then be removed from the deformation chamber and the process repeated after a cycle time in which the bulk material 50 cools to a suitable solidification temperature as discussed above.

Stress Relieving

Following extrusion and optional cooling to a solidification temperature, the bulk material is then preferably stress relieved. In one embodiment, stress relieving is carried out by heating to a stress relief temperature, preferably below the melting point of the polymeric bulk material. If the cooling in the previous step is carried out while maintaining deformation force, the bulk material on stress relieving tends to expand and return to a dimension close to its original dimension. In the non-limiting example of an extruded rod, as the bulk material is heated, the diameter $d_3$ of the rod tends to increase to a diameter approaching $d_1$ of the original bulk material. In various non-limiting embodiments, it has been observed that the bulk material retains about 90-95% of its original dimension upon stress relieving or stress relief heating.

The stress relief process tends to run faster and more efficiently at higher temperatures. Accordingly, stress relief temperatures close to but less than the melting temperature are preferred, for example from the melting point to the melting point minus 30 or 40° C. For UHMWPE, preferred stress relief temperatures include in the range of about 100° C. to about 135° C., 110° C. to about 135° C., 120° C. to 135° C., and preferably 125° C. to about 135° C.

Stress relieving is carried out for a time to complete the stress relief process. In various embodiments, suitable times range from a few minutes to a few hours. Non-limiting examples include 1 to 12 hours, 2 to 10 hours, and 2 to 6 hours in an oven or other suitable means for maintaining a stress relief temperature. Although the stress relieving can be carried out in a vacuum, in an inert atmosphere, or in a package designed to exclude an atmosphere, it is preferably carried out in an air atmosphere.

Under some conditions, the solidified extruded bulk form exhibits a tendency to bend or other deviate from a preferred straight or linear orientation during the heating or other treatment associated with stress relieving. To counter this tendency, in one embodiment, the bulk material is held in a mechanical device that functions to keep the bulk material straight (measured on the axial direction) during the stress relieving step. In a non-limiting example, the bulk material is placed into V-channels to keep them straight. For example, several V-channels are equally spaced from each other and are part of the same physical structure. The several V-channels may, for example, be welded to the structure at equal spacings. The extruded bars are positioned on a bottom set of V-channels and then another set of V-channels is set on top of the extruded bars to rest on top of the bars. These channels help to keep the bars straight during stress relieving.

In various embodiments, the product of the crosslinking, heating, compressing, cooling and stress relieving steps is a bulk material having dimensions approximately equal to the original bulk material before crosslinking. As a result of the steps taken on the bulk material, the bulk material exhibits high tensile strength in the axial direction, a low but detectable level of free radical concentration, and a high degree of resistance to oxidation.

The process described can be followed with regard to the dimensions of the crosslinked polymer at various stages of the process. In various embodiments, a bulk material having an original dimension or diameter of $d_1$ is crosslinked and heated to a compression deformation temperature. The crosslinked heated material is then compressed to a dimension or diameter $d_2$ which is less than $d_1$. In an optional step, the material is then held while cooling at a diameter $d_3$ that may be the same as $d_2$, but in any case is less than the original dimension or diameter $d_1$. After cooling, stress relieving returns the bulk material to a diameter $d_4$ which is greater than $d_3$ and in some embodiments is approximately equal to the original dimension or diameter $d_1$. For example, if the original bulk material is a 3"×14" cylinder of UHMWPE, the treated preform resulting from the steps above preferably typically has a diameter of about 2.7 to 3 inches.

Following the treatment steps described above, the bulk material characterized by an axial direction is machined according to known methods to provide bearing components for implants. In the case of a cylindrical treated bulk material perform, it is preferred first to turn the outer diameter of the cylinder to remove any oxidized outer layers and to provide a straight and round cylinder for further processing. In a preferred embodiment, the cylinder is then cut into billets along the axial direction, and each billet is machined into a suitable bearing component. Preferably, the bearing components are machined from the billets in such a way that the in vivo load bearing axis of the bearing component corresponds to the axial direction of the bulk preform from which it is machined. Machining this way takes advantage of the increased tensile strength and other physical properties in the axial direction of the preform.

For example, in bearing components for joint replacements, the stresses at the bearing surface are typically multiaxial, and the magnitude of the stresses further depends on the conformity of the joint. For hip applications, the polar axis of the cup is aligned with the longitudinal axis of the extruded rod, corresponding to the axial direction. The wall of the cup, at the equator and rim, is parallel to the long axis of the rod, and will benefit from the enhanced strength in this direction during eccentric and rim loading scenarios.

Oxidative Resistance

It has been found that UHMWPE, preforms, and bearing components made according to the invention have a high level of oxidative resistance, even though free radicals can be detected in the bulk material. To measure and quantify oxidative resistance of polymeric materials, it is common in the art to determine an oxidation index by infrared methods such as those based on ASTM F 2102-01. In the ASTM method, an oxidation peak area is integrated below the carbonyl peak between 1650 cm$^{-1}$ and 1850 cm$^{-1}$. The oxidation peak area is then normalized using the integrated area below the methane stretch between 1330 cm$^{-1}$ and 1396 cm$^{-1}$. Oxidation index is calculated by dividing the oxidation peak area by the normalization peak area. The normalization peak area accounts for variations due to the thickness of the sample and the like. Oxidative stability can then be expressed by a change in oxidation index upon accelerated aging. Alternatively, stability can be expressed as the value of oxidation attained after a certain exposure, since the oxidation index at the beginning of exposure is close to zero. In various embodiments, the oxidation index of crosslinked polymers of the invention changes by less than 0.5 after exposure at 70° C. to five atmospheres oxygen for four days. In preferred embodiments, the oxidation index shows a change of 0.2 or less, or shows essentially no change upon exposure to five atmospheres oxygen for four days. In a non-limiting example, the oxidation index reaches a value no higher than 1.0, preferably no higher than about 0.5, after two weeks of exposure to 5 atm oxygen at 70° C. In a preferred embodiment, the oxidation index attains a value no higher than 0.2 after two or after four weeks exposure at 70° to 5 atm oxygen, and preferably no higher than 0.1. In a particularly preferred embodiment, the specimen shows essentially no oxidation in the infrared spectrum (i.e. no development of carbonyl bands) during a two week or four week exposure. In interpreting the oxidative stability of UHMWPE prepared by these methods, it is to be kept in mind that the background noise or starting value in the oxidation index determination is sometimes on the order of 0.1 or 0.2, which may reflect background noise or a slight amount of oxidation in the starting material.

Oxidation stability such as discussed above is achieved in various embodiments despite the presence of a detectable level of free radicals in the crosslinked polymeric material. In various embodiments, the free radical concentration is above the ESR detection limit of about 0.06×10$^{15}$ spins/g and is less than that in a gamma sterilized UHMWPE that is not subject to any subsequent heat treatment (after sterilization) to reduce the free radical concentration. In various embodiments, the free radical concentration is less that 3×10$^{15}$, preferably less 1.5×10$^{15}$, and more preferably less than 1.0×10$^{15}$ spins/g. In various embodiments, the oxidation stability is comparable to that of melt processed UHMWPE, even if according to the invention the UHMWPE is processed only below the melting point.

Although the invention is not to be limited by theory, the free radicals in the deformation processed UHMWPE described above may be highly stabilized and inherently resistant to oxidative degradation. Alternatively or in addition, they may be trapped within crystalline regions of the bulk material and as a consequence may be unavailable to participate in the oxidation process. Because of the oxidation stability of the material, in various embodiments it is justifiable to employ gas permeable packaging and gas plasma sterilization for the extrusion processed radiation UHMWPE. This has the advantage of avoiding gamma sterilization, which would tend to increase the free radical concentration and lead to lower oxidation stability.

In various embodiments, the solid state deformation process provides polymers that are characterized by a crystal and molecular orientation. By molecular orientation is meant that polymer chains are oriented perpendicular to the direction of compression. By crystalline orientation it is meant that crystal planes in polyethylene, such as the 200 plane and the 110 plane are oriented to the direction parallel to the compression plane. In this way the crystal planes are oriented. The presence of the orientations can be shown by means of birefringent measurements, infrared spectra, and x-ray diffraction.

The plane of compression for articles compressed in a radial direction is understood to be a surface surrounding and parallel to the radial surface of the bulk material that is processed according to the invention. In the non-limiting example of a cylindrical rod, a sequence of circular cross sections along the axial direction defines a radial surface and a compression plane perpendicular to that surface. In response to compression around the radial plane, polymer chains orient themselves perpendicular to the direction of compression. This has the effect in a cylinder of providing molecular orientation generally parallel to the radial plane. It is believed that with this molecular and crystal orientation contributes to the enhancement of mechanical properties, and to anisotropy in the mechanical properties with respect to the axial and transverse (or radial) directions.

In various embodiments, crosslinked UHMWPE are provided that exhibit a high level of tensile strength in at least one direction. Advantageously, bearing components and implants are provided that take advantage of the increased strength of the bearing material. For example, in crosslinked UHMWPE, it is possible to achieve a tensile strength at break of at least 50 MPa, preferably at least 55 MPa, and more preferably at least 60 MPa. In various embodiments, materials are provided with a tensile strength at break in the range of 50-100 MPa, 55-100 MPa, 60-100 MPa, 50-90 MPa, 50-80 MPa, 50-70 MPa, 55-90 MPa, 55-80 MPa, 55-70 MPa, 60-90 MPa, 60-80 MPa, and 60-70 MPa. In a non-limiting embodiment the tensile strength of a UHMWPE prepared according the invention is about 64 MPa in the axial direction.

EXAMPLES

Comparative Example

Isostatically molded UHMWPE bar stock (Ticona, Inc., Bishop, Tex.) is packaged in an argon environment and gamma sterilized to a dose of 25 to 40 kGy

Example 1

Radiation crosslinked, deformation processed UHMWPE is produced using the following steps:

1. Radiation crosslinking. Isostatically molded UHMWPE rods of dimensions 3"×14" (Ticona, Inc., Bishop, Tex.) are vacuum packed in a foilized bag and gamma radiation crosslinked with a nominal dose of 50 kGy.

2. Preheating. Prior to deformation processing, the rod is removed from the foilized bag and raised to 133° C. for 4 to 12 hours in an oven.

3. Solid state, hydrostatic extrusion. The heated rod is then removed from the oven and placed in the holding chamber of a press. The temperature of the holding chamber is 130° C.±5° C. The bar is then ram extruded using a sacrificial puck made of crosslinked UHMWPE through a circular die, into a cooling chamber with a diametral compression ratio of 1.5 (diameter of 3" down to 2").

4. Cooling and solidification. The cooling chamber is sized so as to maintain the extruded rod in a deformed state. The walls of the cooling chamber are water-cooled. When thermocouples embedded in the wall (about 1 mm from the inside wall) read 30° C., the solidified rod is removed, optionally after an additional cooling period of ten minutes, in a non-limiting example. If desired, a second bar is ram extruded to eject the cooled bar from the cooling chamber, once the temperature reaches about 30° C.

5. Stress relief annealing. The deformed rod is then heated at 133±2° C. for 5 hours. The annealing also improves dimensional stability in the material. The rod is then slowly cooled to room temperature. The extruded rod retains about 90-95% of its initial diameter after the stress relief step.

6. Gas plasma sterilization. After cooling, a liner or other bearing material is machined and the machined part is non-irradiatively sterilized (e.g., with ethylene oxide or gas plasma)

Specimen Preparation and Orientation

For compression tests and accelerated aging, right rectangular prism specimens are evaluated. The specimens measure 12.7 mm by 12.7 mm by 25.4 mm (0.50 in. by 0.50 in. by 1.00 in.) They are machined from the rod stock parallel (the axial direction) or perpendicular (the transverse direction) to the long axis.

For tensile tests, dumbbell-shaped tensile specimens consistent with the Type IV and V specimen description provided in ASTM D638-02a are tested. Specimens are 3.2±0.1 mm thick. Specimens are oriented parallel or perpendicular to the long axis, reflecting the axial and transverse directions, respectively).

Physical and Mechanical Properties

Tensile strength at break is determined according to ASTM 638-02a.

The concentration of free radicals in the UHMWPE materials is characterized using an ESR spectrometer (Bruker EMX), as described previously in Jahan et al., J. Biomedical Materials Research, 1991; Vol. 25, pp 1005-1017. The spectrometer operates at 9.8 GHz (X Band) microwave frequency and 100 kHz modulation/detection frequency, and is fitted with a high sensitivity resonator cavity. For a good spectral resolution and/or signal-to-noise ratio, modulation amplitude is varied between 0.5 and 5.0 Gauss, and microwave power between 0.5 and 2.0 mW.

Accelerated Aging

Specimens are aged in 5 atmospheres of oxygen in accordance with ASTM F 2003-00. Some specimens are aged for two weeks according to this standard, and others are aged for four weeks. Aging is performed in a stainless steel pressure vessel. The specimens are chosen and oriented such that the tested axis is vertical. Thus, the top and bottom faces are perpendicular to the test axis. The top face is labeled for later identification. The vessels are then filled with oxygen and purged five times to ensure the purity of the aging environment. The prisms rest on a flat surface inside the pressure vessel; thus each prism's bottom face is not exposed to oxygen, but each of its other faces are exposed to oxygen throughout the aging period.

The vessel is placed in the oven at room temperature (24±2° C.), and the oven was heated to the aging temperature of 70.0±0.1° C. at a rate of 0.1° C./min.

FTIR Analysis

Materials are evaluated before and after accelerated aging by Fourier transform infrared spectroscopy (FTIR) in transmission (Excalibur series FTS3000 with a UMA-500 microscope attachment; Bio-Rad Laboratories, Hercules, Calif.). FTIR profiling is conducted perpendicular to the transverse direction.

Oxidation index measurement and calculations are based on ASTM F 2102-01. Oxidation peak area is the integrated area below the carbonyl peak between 1650 and 1850 cm$^{-1}$. The normalization peak area is the integrated area below the methylene stretch between 1330 and 1396 cm$^{-1}$. Oxidation index is calculated by dividing the oxidation peak area by the normalization peak area.

Results

Data for the Comparative Example and Example 1 are given in the Table

|  | Comparative Example | Example 1 | Example 1, axial | Example 1, transverse |
|---|---|---|---|---|
| Tensile Strength at Break [MPa] | 46.8 ± 2.0 |  | 64.7 ± 4.5 | 46.1 ± 3.5 |
| Free radical concentration, spins/g | 3.82 × 10$^{15}$ | 0.22 × 10$^{15}$ |  |  |
| Oxidation index before aging (at surface) | 0.2 | <0.1 |  |  |
| Oxidation index after aging (at surface) | 1.2 | <0.1 |  |  |

Although the invention has been described above with respect to various embodiments, including those believed the most advantageous for carrying out the invention, it is to be understood that the invention is not limited to the disclosed embodiments. Variations and modifications that will occur to one of skill in the art upon reading the specification are also within the scope of the invention, which is defined in the appended claims.

We claim:

1. A method for preparing a UHMWPE pre-form suitable for use in medical implants comprising
   heating a gamma-crosslinked UHMWPE rod characterized by a crystalline melting point and a diameter $d_1$ to a compression deformable temperature;
   applying compression force on the crosslinked UHMWPE to reduce the diameter to $d_2$, wherein $d_2<d_1$;
   cooling the reduced diameter rod of UHMWPE to a solidification temperature while maintaining compression force to keep the diameter at a diameter of $d_3$, wherein $d_3<d_1$; and
   stress relieving the cooled rod by heating to a temperature at which the rod expands to a diameter $d_4$, wherein $d_4>d_3$, and wherein $d_4$ is approximately equal to $d_1$.

2. A method according to claim 1, comprising extruding the rod through a reducing die into a cooling chamber to reduce the diameter from $d_1$ to $d_2$.

3. A method according to claim 1, wherein the compression deformable temperature is from the melting point minus 50° C. to the melting point.

4. A method according to claim 1, wherein the compression deformable temperature is less than the melting point.

5. A method according to claim 1, wherein the compression deformable temperature is from about 100° C. to about 135° C.

6. A method according to claim 1, wherein the compression deformable temperature is about 125° C. to 135° C.

7. A method according to claim 1, wherein the UHMWPE rod is crosslinked by gamma-irradiation at a dose of 0.01-10 Mrad.

8. A method according to claim 1, wherein the UHMWPE rod is crosslinked by gamma-irradiation at a dose of 1-6 Mrad.

9. A method according to claim 1, wherein the UHMWPE rod is crosslinked by gamma-irradiation at a dose of 2-5 Mrad.

10. A method according to claim 1, wherein $d_3$ is approximately equal to $d_2$.

11. A method according to claim 1, wherein the UHMWPE is gamma-irradiated at a dose of 1-5 Mrad, the compression deformable temperature is greater than 100° C. and less than the melting point, applying compression force comprises extruding the heated crosslinked UHMWPE through a reducing die, the rod is cooled to a temperature of 30° C. or less after extrusion, and stress relieving is carried out at a temperature of 100° C. to 130° C.

12. A method for making a UHMWPE implant bearing component, comprising machining the component from a pre-form made according to claim 1.

13. A method for making a UHMWPE implant bearing component, comprising machining the component from a pre-form made according to claim 11.

14. A method for preparing a UHMWPE pre-form suitable for use in medical implants comprising
heating a gamma-crosslinked UHMWPE rod characterized by a crystalline melting point and a diameter $d_1$ to a compression deformable temperature below the crystalline melting point;
applying compression force on the crosslinked UHMWPE to reduce the diameter to $d_2$, wherein $d_2 < d_1$;
cooling the reduced diameter rod of UHMWPE to a solidification temperature while maintaining compression force to keep the diameter at a diameter of $d_3$, wherein $d_3 < d_1$; and
stress relieving the cooled rod by heating to a temperature below the crystalline melting point at which the rod expands to a diameter $d_4$, wherein $d_4 > d_3$, and wherein $d_4$ is approximately equal to $d_1$.

15. A method according to claim 14, comprising extruding the rod through a reducing die using a sacrificial puck made of crosslinked UHMWPE.

16. A method according to claim 14, wherein the UHMWPE rod is crosslinked by γ-irradiation at a dose of 0.01 to 10 MRad.

17. A method according to claim 14, wherein the UHMWPE rod is crosslinked by γ-irradiation at a dose of 1 to 6 MRad.

18. A method according to claim 14, wherein $d_3$ is approximately equal to $d_2$.

19. A method according to claim 14, wherein the draw ratio $d_1/d_2$ is from 1.1 to 3.0.

20. A method according to claim 14, wherein the draw ratio $d_1/d_2$ is from 1.2 to 3.0.

21. A method according to claim 14, wherein the draw ratio $d_1/d_2$ is from 1.2 to 1.8.

22. A method according to claim 14, wherein the draw ratio $d_1/d_2$ is from 1.2 to about 1.5.

23. A method according to claim 14, wherein the draw ratio $d_1/d_2$ is greater than 1 and less than or equal to 2.5.

24. A method according to claim 14, wherein the draw ratio $d_1/d_2$ is greater than 1 and less than or equal to about 2.0.

25. A method for preparing a UHMWPE preform suitable for use in medical implants, comprising
heating a γ-crosslinked UHMWPE rod characterized by a crystalline melting point and a diameter $d_1$ to a compression deformable temperature less than the melting point;
extruding the heated crosslinked UHMWPE through a reducing die to reduce the diameter to $d_2$, wherein $d_2$ less than $d_1$;
cooling the reduced diameter rod of UHMWPE to a solidification temperature while maintaining compression force to keep the diameter at a diameter of $d_3$, wherein $d_3$ less than $d_1$; and
stress relieving the cooled rod by heating to a temperature at which the rod expands to a diameter $d_4$, wherein $d_4$ is greater than $d_3$, and where $d_4/d_1$ is from 0.9 to 1.0.

26. A method according to claim 25, comprising extruding the rod through a reducing die using a sacrificial puck made of crosslinked UHMWPE.

27. A method according to claim 25, wherein the compression deformable temperature is from about 100° C. to 135° C.

28. A method according to claim 25, wherein the compression deformable temperature is about 125° C. to 135° C.

29. A method according to claim 25, wherein the UHMWPE rod is crosslinked by γ-irradiation at a dose of 0.01 to 10 MRad.

30. A method according to claim 25, wherein the UHMWPE rod is crosslinked by γ-irradiation at a dose of 1 to 6 MRad.

31. A method according to claim 25, wherein stress relieving is carried out at a temperature below the melting point.

32. A method according to claim 25, wherein the draw ratio $d_1/d_2$ is from 1.1 to 3.0.

33. A method according to claim 32, wherein the draw ratio is less than or equal to 2.5.

34. A method according to claim 32, wherein the draw ratio is less than or equal to 2.0.

35. A method for making a UHMWPE implant bearing component, comprising machining the component made from a preform according to claim 34.

36. A method for making an implant bearing component preform according to the method of claim 34 and machining the preform to make the component.

37. A method according to claim 32, wherein the draw ratio is from 1.2 to 1.8.

38. A method for making a UHMWPE implant bearing component comprising machining the component from a preform made according to claim 25.

39. A method for making an implant bearing component, comprising making a preform according to the method of claim 25 and machining the preform to make the component.

* * * * *